United States Patent [19]

Strong et al.

[11] Patent Number: 5,596,268
[45] Date of Patent: *Jan. 21, 1997

[54] METHOD AND APPARATUS FOR DETERMINING EXTENT OF CURE IN POLYMERS

[75] Inventors: A. Brent Strong, Sandy; R. Scott Merrell; Barry M. Lunt, both of Provo, all of Utah

[73] Assignee: Brigham Young University, Provo, Utah

[*] Notice: The term of this patent shall not extend beyond the expiration date of Pat. No. 5,432,435.

[21] Appl. No.: 493,796

[22] Filed: Jun. 22, 1995

Related U.S. Application Data

[63] Continuation of Ser. No. 948,008, Sep. 22, 1992, Pat. No. 5,432,435.
[51] Int. Cl.[6] ............................ G01N 27/02; G01R 27/16
[52] U.S. Cl. .......................... 324/71.1; 324/693; 324/705
[58] Field of Search .................................... 324/71.1, 691, 324/693, 705, 706, 714, 723

[56] References Cited

U.S. PATENT DOCUMENTS

| | | |
|---|---|---|
| 3,791,792 | 2/1974 | Lindsay . |
| 4,129,824 | 12/1978 | Howes . |
| 4,710,550 | 12/1987 | Kranbuehl . |
| 4,777,431 | 10/1988 | Day et al. . |
| 4,891,591 | 1/1990 | Johnston et al. . |
| 5,089,780 | 2/1992 | Megerle . |
| 5,095,278 | 3/1992 | Hendrick . |
| 5,184,077 | 2/1993 | Day et al. . |
| 5,200,027 | 4/1993 | Lee et al. . |
| 5,210,449 | 5/1993 | Walsh . |
| 5,432,435 | 7/1995 | Strong et al. ............................ 324/693 |

OTHER PUBLICATIONS

In–Process Controlled Curing Of Resin Matrix Composites by Michael J. Yokota Date Unavailable.

Dielectric Analysis Of Thermoset Cure by Stephen D. Senturia and Norman F. Sheppard, Jr. 1986 pp. 1–47, Advances in Polymer Science 80, Springer–Vertag Berlin Heidelberg.

*Primary Examiner*—Kenneth A. Wieder
*Assistant Examiner*—Glenn W. Brown
*Attorney, Agent, or Firm*—Thorpe, North & Western

[57] ABSTRACT

A method for detecting extent of cross-linking of a high impedance polymer material during a pre-cure stage, the method comprising the steps of:

a) applying a test signal through a sensor to the polymer material in the pre-cure stage to determine a level of impedance and corresponding sample voltage representative of a degree of cross-linking within the material;

b) applying the same test signal through the sensor to a reference material having a fixed resistance to determine a reference voltage;

c) determining a voltage difference between the test signal applied to the polymer at pre-cure stage and the test signal applied to the reference material as the reference voltage;

d) correlating the voltage difference as a relative indicator of the extent of cross-linking which has occurred within the polymer material, based on comparison of magnitude of the voltage difference with respect to a comparable potential range of impedance for the polymer material from its lower impedance stage at minimal cross-linking to its high impedance stage at maximum impedance for total cross-linking.

24 Claims, 4 Drawing Sheets

METHOD AND APPARATUS FOR DETERMINING EXTENT OF CURE IN POLYMERS

This application is a continuation of application Ser. No. 07/948,008, filed Sep. 22, 1992 now U.S. Pat. No. 5,432,435.

BACKGROUND OF THE INVENTION

The present invention relates to a METHOD AND APPARATUS FOR DETERMINING EXTENT OF CURE IN POLYMERS.

1. Field of Invention

This invention relates to a process for determining the extent of cross-linking which has occurred in a polymeric material such as paint, dental resin, B-staged resin, etc. More particularly, the present invention pertains to the detection of extent of curing of such materials in their pre-cure stage.

2. Prior Art

Thermosetting resins form a class of very useful plastics which have been applied throughout the aerospace industry, construction industry, automotive manufacturing, medical applications, adhesives, and in virtually every area where permanent characteristics of weatherability, structural stiffness, strength and ease of manufacture through molding process provides an advantage over competing metals, ceramics and other compositions. Dental applications include filling and facia materials which are applied to the tooth in liquid form and then polymerized by UV radiation or other known techniques. Many paint compositions are a form of thermosetting resin whose application depends on having a uniform liquid state which can be readily applied by brush or air gun. Matched die, filament winding, transfer molding, lay up molding and pultrusion techniques for fabricating structural and component parts, housings, etc., depend on maintenance of a flowable condition which can wet fibers or quickly fill mold cavities in a liquid state.

These resin materials are typically manufactured in a low viscous liquid state wherein the polymer material has incurred minimal cross-linking prior to the curing stage. It is, of course, this cross-linking that solidifies the thermosetting composition into a permanent, rigid structure characterizing this group of plastics. The shelf life of such products is significant, because premature curing results in permanent, irreversible condition which makes the material useless for further processing. Indeed, the extent of waste arising because of premature curing of thermosetting materials is substantial. In industries where partially cured materials must be discarded for safety reasons, the losses are even more significant. For example, the manufacture of high performance aircraft components from resins that have already partly cured could result in weakened structures that put life in jeopardy. Therefore, it is very likely that a substantial amount of good resin is discarded because of suspicion of excessive pre-cure.

Because most resins will inherently begin cross-linking upon manufacture and will continue such cross-linking until finally cured, measures are taken to reduce and control this process. The primary control measure is to maintain the resins at low temperatures to reduce reaction rates to a minimum. This low temperature environment needs to be maintained until the material is ready for final curing. Unfortunately, the resin material appearance does not always reflect the degree of curing which has occurred during this pre-cure stage. If variations in temperature occur during storage, their impact may be substantially unknown. Therefore, the extent of cure is often a risk factor that must be considered with the choice of any particular resin.

With paints and adhesives, viscosity provides a useful measure of acceptability of pre-cure. In general, their shelf life is determined by the time required for the material to set up or become too viscous to flow well. There are, however, no current tests to determine the actual state of cross-linking in paints and adhesives. Current practice is to examine the viscosity of the materials qualitatively as noted, or perform sample tests to determine the performance of these resins in a particular application.

With respect to polymers used in a matrix material for fiber reinforced composites, there are two distinct time periods during which cross linking takes place. The first period can be called the shelf life of the material and the second is the curing cycle. Typically, thermosetting resins for composites are stored at very low temperatures such as –0 degrees F. The curing cycle occurs when the resins are subjected to heat/radiation and/or pressure during molding processes. For example, elevated temperatures in the range of 200 to 400 degrees F, and occasionally as high as 700 degrees F, are common for curing these polymers and can enable the completion of cross linking in a short time interval.

Users of fiber reinforced thermosetting composites have created several mechanical tests to evaluate the state of cumulative cross linking in the storage and pre-cure stages. For example, tack and drape properties give an indication of the extent of cure. These tests are acknowledged to be highly subjective and unreliable, and are at best general qualitative indicators having little quantitative value.

A more specific application of thermosetting resins for composite materials is to impregnate a layer of fiber reinforcement with resin, and then store this "pre-preg" or "B-staged" material for later use. Obviously, this B-staged material will have a limited shelf life, depending upon the rate of continued cross linking, which is affected mainly by temperature. It is presently difficult, subjective, and consumptive of material to test the B-staged material for the extent of cross linking. If the B-staged material has reached a particular stage of cross linkage, it is no longer usable material and must be discarded on the basis of storage time, rather than on the actual amount of cross linking.

There is increasing interest in the composites industry to monitor, adjust and optimize the cure cycle of thermoset polymers. Accordingly, it is known to evaluate cross linking during actual cure using viscometers, infrared meters, and microdielectrometers. This period of evaluation is characterized by the resins being subjected to high temperatures used to fully complete the curing of the materials. The primary interest is to identify the gelation point and then to confirm final stage at which the curing process is complete, so that the final product can be removed without extending cure time and conditions beyond that which is necessary. This enables efficient use of expensive equipment and also insures that the manufactured part is not removed from the mold prior to complete cross linking.

The present inventors are unaware of any activity designed to determine the extent of cross linking in polymers prior to the actual curing process within a high temperature environment. Specifically, adhesives and paints represent a broad class of polymers which do not require devoted temperatures to cure to final stage. Because curing in such polymers is an ongoing process at a somewhat continuous rate, neither intermediate nor final cure status is generally measured. Where polymers are cured in two stages representing pre-cure and elevated final process, the only point of measurement of cross linking in polymers has occurred only during the elevated conditions, with little regard for cross linking during the pre-cure stage or shelf-life period.

This practice may have arisen in part from an assumption that the electrical response of any polymer at low temperatures applied during storage would not provide enough signal to show a measurable change as the pre-cure cross linking continues.

What is needed is an effective method for detecting the extent of cure in polymer materials during the shelf-life period, to enable more effective determination of whether specific batches or lots of polymer have exceeded safe limits in the pre-cure stage. Such procedures could provide quantitative determination of which resins must be discarded and which can be safely used, and yield substantial savings in cost and natural resources.

OBJECTS AND SUMMARY OF THE INVENTION

It is an object of the present invention to provide a device and method for enabling the determination of the extent of cross linking in any resistive polymer.

It is yet another object of this invention to provide a device and method as stated above which can be effectively applied during the pre-cure stage of a polymer, wherein the polymer is maintained at low temperatures for minimizing cross linking.

A further object of the present invention is to provide a method and system for providing ongoing or continuous detection of cross linking within a pre-cure polymer, which can be applied to paints, adhesives, caulking, dental resins, resins for composites and molding systems.

Yet another object of this invention is to provide the objects noted above within a low cost system which is convenient to use under virtually all situations.

These and other objects are realized in a method for detecting extent of cross-linking of a high impedance polymer material during a pre-cure stage at low temperature. This method includes the steps of:

a) applying a test signal through a sensor to the polymer material in the pre-cure stage to determine a level of impedance and corresponding sample voltage representative of a degree of cross-linking within the material;

b) applying the same test signal through the sensor to a reference material having a fixed resistance to determine a reference voltage;

c) determining a voltage difference between the test signal applied to the polymer at pre-cure stage and the test signal applied to the reference material as the reference voltage; and d) correlating the voltage difference as a relative indicator of the extent of cross-linking which has occurred within the polymer material, based on comparison of magnitude of the voltage difference with respect to a comparable potential range of impedance for the polymer material from its lower impedance stage at minimal cross-linking to its high impedance stage at maximum impedance for total cross-linking.

Another aspect of this invention is represented by a device for testing extent of cross-linking of a polymer material in a pre-cure stage, wherein the device comprises a signal generator capable of generating a low frequency, low amplitude signal with an attached sensor adapted for receiving a coating of the polymer material to be tested, wherein the sensor has a known impedance. A reference material is provided which has a resistance approximately equal to the geometric mean of (i) the impedance of the sensor with polymer material in its lower-resistivity state, and (ii) the expected impedance of the polymer material when the polymer material has reached its high resistivity state upon full curing. The device includes voltage means for determining voltage difference between a signal detected through the sensor with polymer material and a signal detected through the sensor at the reference material. Means are provided and coupled to the voltage means for converting the voltage difference to a factor representing the extent of cross-linking which has occurred within the polymer material.

Other objects and features of the present invention will become apparent to those skilled in the art, based upon the following detailed description of a preferred embodiment, taken in combination with the accompanying drawings.

DETAILED DESCRIPTION OF THE INVENTION

Figure 1:
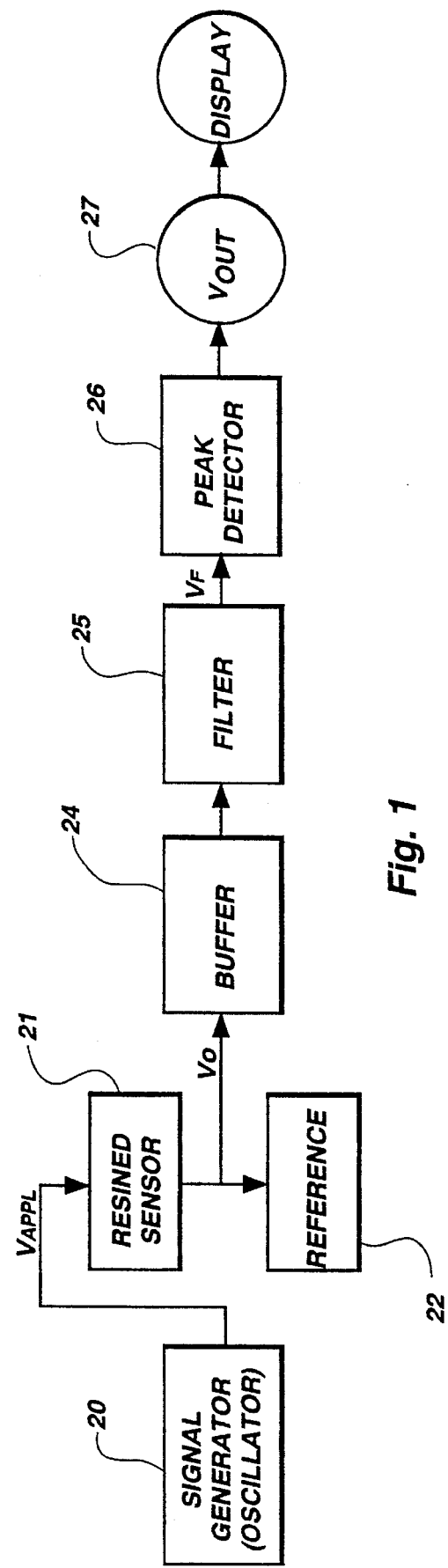
FIG. 1 shows a graphic, block diagram of the various functional features of the present invention.

The present inventors have discovered that it is possible to determine the extent of cross-linking in any resistive polymer, even during the pre-cure stage.

Specifically, the invention comprises a method for detecting extent of cross-linking of a high impedance polymer material during a pre-cure stage. The first step of this method involves applying a test signal through a sensor to the polymer material in the pre-cure stage to determine a level of impedance and corresponding sample voltage representative of a degree of cross-linking within the material. Typically, this signal will be an electric current whose amplitude is inversely proportional with the resistance of the polymer in accordance with Ohms law $I=E/R$. Other techniques of measuring the resistance of the material may likewise be employed.

The test signal is conducted directly into the polymer by means of an interdigitated electrode sensor which is inserted in contact with the polymer. Other than the interdigitated relationship of the electrodes, the geometry of the probe is not significant. Any conductive material coupled at one end to a voltage source may be used as a probe. Where the sensor is used with high resistivity resins, the probe should be shielded by a shielding means coupled around the sensor to shield from static electricity.

The next step of this methodology is applying the same test signal as applied in the previous step through the sensor to a reference material, such as a fixed value resistor. This provides the quantitative character of the procedure. The reference material should have a fixed resistance to determine a reference voltage. A voltage difference between the test signal applied to the polymer at pre-cure stage and the test signal applied to the reference material as the reference voltage is then determined. This voltage difference serves as a relative indicator of the extent of cross-linking which has occurred within the polymer material, based on comparison of magnitude of the voltage difference with respect to a comparable potential range of impedance for the polymer material from its lower impedance stage at minimal cross-linking to its high impedance stage at maximum impedance for total cross-linking.

The mechanics of processing the voltage difference to get an indication of the actual extent of cross-linking may vary. The preferred technique represented in the disclosed figures involves converting the alternating voltage to direct current and inputting this direct current to a display device which gives direct readout of a value which can be correlated with the extent of cross-linking of the polymer. This direct readout comprises a DC voltage ranging from approximately 0.5 volts at low impedance to 0.0 at high impedance, representing a range of magnitude of at least approximately $1 \times 10^4$. This may extend as high as $10^8$.

The test signal is applied by generating a low frequency signal of less than 10 Hz, having a low amplitude of less than 20 volts peak to peak, and by applying this signal to the polymer in uncured stage and to the reference resistance. In a more preferred embodiment, the low frequency signal is approximately 0.1 Hz to 5 Hz, and consists of a low amplitude of less than 10 volts peak to peak.

Figure 2A:
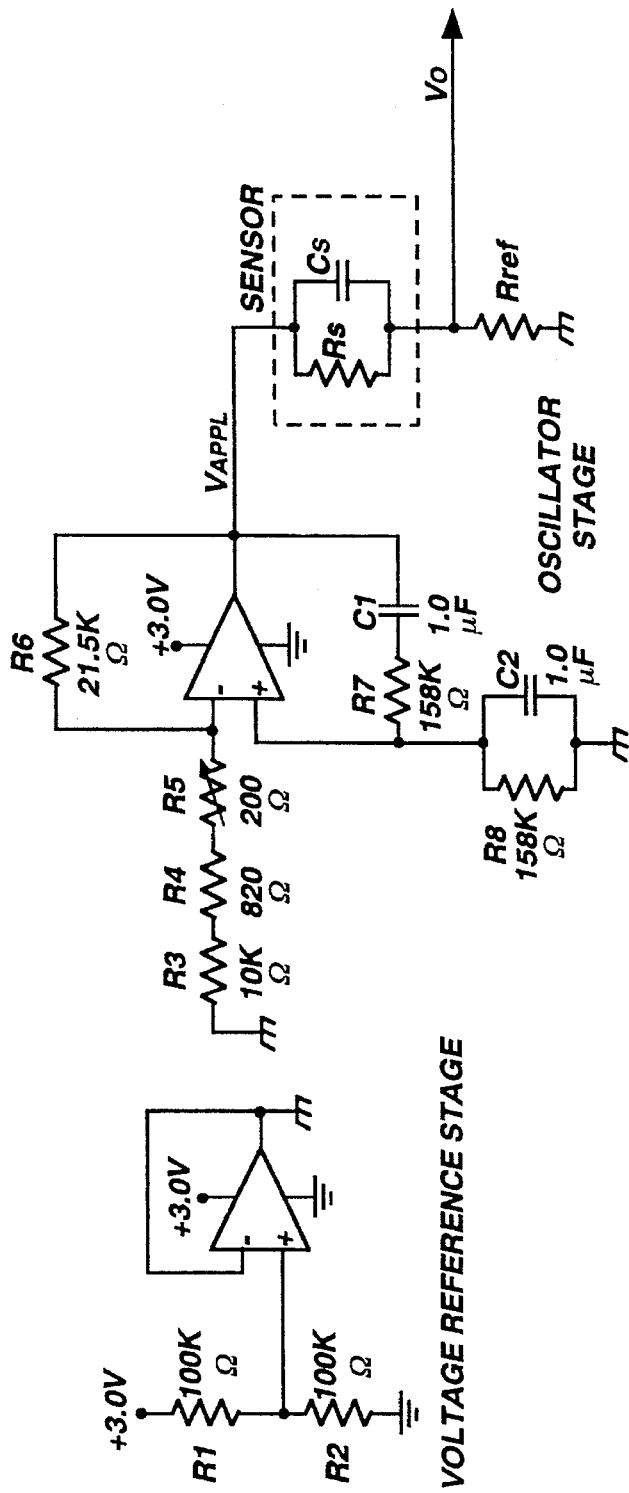
FIG. 2 shows a schematic diagram of circuitry providing a preferred embodiment of the present invention.
Figure 2B:
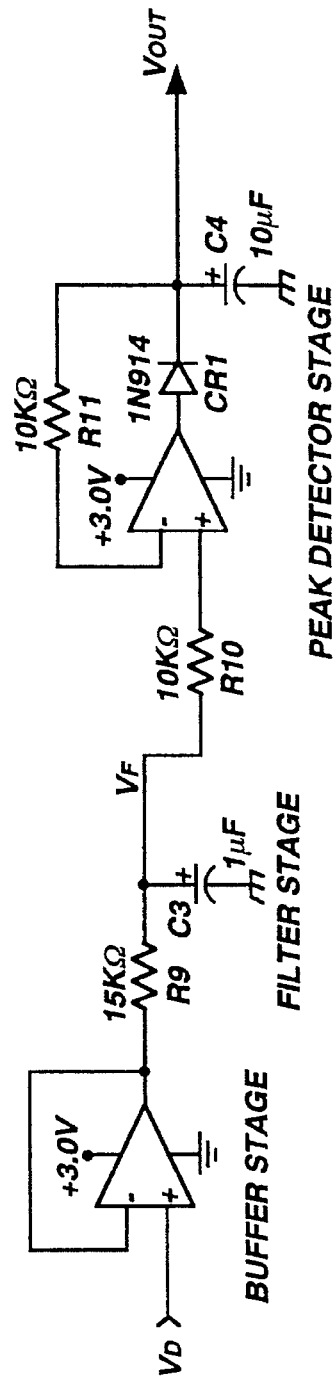

FIGS. 1 and 2 illustrate implementation of this invention by structuring the polymer material and the reference material within the circuit as a voltage divider wherein the voltage output is proportional to the ratio of the impedance of the reference material to total impedance of the polymer material plus the reference material. This circuit can sense a resistance change in the order of $10^4$ Ohms from the fresh stage of the material to the cured stage. Such a range is typical for resins, plastics, paints, adhesives and caulks. In addition the circuit can be adjusted to begin sensing in the fresh stage at anywhere from $10^3$ Ohms to $10^8$ Ohms, finishing up in the cured stage at anywhere from $10^7$ Ohms to $10^{13}$ Ohms.

FIG. 1 shows a block diagram in which the signal generator 20 is a sinusoidal generator which provides a 1 Hz, 1 Volt p-p signal (Vappl) which is applied to the sensor 21 and coated polymer to be tested. This signal is then applied to the reference resistor 22. The voltage between these function blocks (Vd) is then buffered 24 and filtered 25, after which the resulting signal (Vf) is converted to DC with a peak detector 26. V(out) 27 is then a DC voltage ranging from approximately 0.5 volts (for lower resistivity) up to 0 volts (for high-resistivity). The illustrated circuit can sense a range of about $1 \times 10^4$ Ohms.

Figure 3:
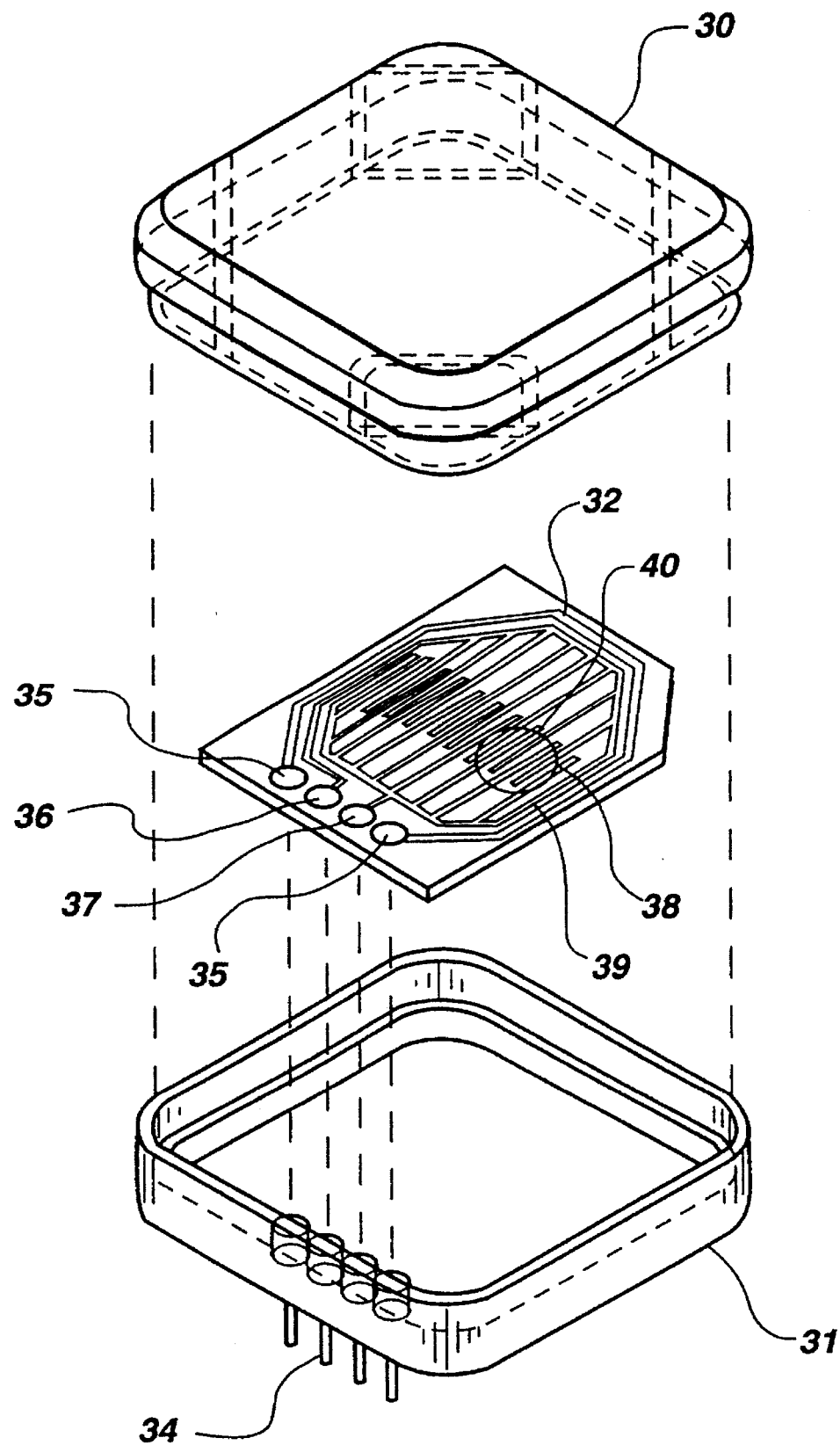
FIG. 3 shows an exploded view of a sensor device useful with the disclosed circuitry for monitoring extended preliminarization.

An important part of this sensor is the resin-covered sensor combined with the reference. One embodiment of the sensor is shown in FIG. 3. This device comprises an upper 30 and lower 31 casement, with the interdigitated electrode sensor component 32 enclosed therein. Contact pins 34 are electrically coupled to contacts 35, 36, and 37 of the sensor component. Contacts 35 are at ground potential, while contacts 36 and 37 provide the voltage differential V(subscript D) for indicating the extent of polymerization. These contacts 36 and 37 are coupled to the respective interdigitated terminal electrode 38 and 39. The actual measurement of resistivity is made by placing the polymer 40 to be tested on two or more of the adjacent terminal electrodes 38 and 39 to provide a conductance path for measuring resistance through the material. This grid of interdigitated electrodes may be etched or plated on a substrate in accordance with standard technology. The pins 34 are coupled by wires to appropriate contacts of the circuitry described in FIG. 2.

The reference sensor 22 is simply a fixed-value resistor chosen to be approximately equal to the geometric mean of the impedance of the sensor with material in its lower resistivity state, and the same impedance as expected when the material has reached its high resistivity state. In this manner, the sensor and the reference form a simple voltage divider. The output voltage from this divider is proportional to the ratio of the reference resistor to the total impedance of the sensor plus the reference resistor, as shown in Equation 1:

$$Vd \propto \frac{Rr}{Rr + Zs}$$

Vd=Voltage divider output voltage
Rr=Reference resistor
Zs=Impedance

Specific considerations are relevant to FIG. 2. For example, the purpose of the voltage reference stage is simply to allow the remaining op amp stages to operate in a pseudo-dual-supply mode. This is necessary because the circuit is to be battery powered, yet generate an AC signal with no DC offset as applied to the sensor. Resistor R5 is a multi-turn trim potentiometer. It is necessary to adjust the gain of the oscillator to the point where a steady amplitude signal is produced.

The op amp chosen must have an input impedance in the area of $10^{12}$ Ohms and must operate from +3 volts. The op amp chosen for the test implementation of this invention was the Texas Instruments TSC27M4AIN. The buffer stage is necessary to prevent loading the voltage divider output voltage, Vd. The buffer stage raises the load impedance to about $10^{15}$ Ohms. The filter stage is an attempt to limit the bandwidth of the entire circuit and thereby reduce noise sensitivity to most stray voltages and all static electricity. For this reason, the enclosure should be carefully shielded.

When energized, the oscillator stage may not automatically start oscillating and may require a jump-start. This is accomplished by simply disconnecting R8 from the reference ground voltage, and reconnecting it. It should also be noted that V(out) will not change quickly. Therefore, when testing a new or different sensor, C4 should be momentarily shorted out, then returned to normal. This will allow V(out) to settle more quickly to its final value.

The above described structure is representative of a device for testing the extent of cross-linking of a polymer material in a pre-cure stage which is generally described to include (i) a signal generator capable of generating a low frequency, low amplitude signal; (ii) a sensor coupled to the signal generator and adapted for receiving a coating of the polymer material to be tested, the sensor having a known impedance; (iii) a reference material which has a resistivity approximately equal to the geometric mean of the impedance of the sensor with polymer material in its lower-resistivity state, and the expected impedance of the polymer material when the polymer material has reached its high resistivity state upon full curing; and voltage means for determining the voltage difference between a signal detected through the sensor with polymer material and a signal detected through the sensor at the reference material. Converting means is coupled to the voltage means for converting the voltage difference to a factor representing the extent of cross-linking which has occurred within the polymer material. A display means may be coupled to the converting means to provide a visual readout of the extent of cross-linking in real time mode.

Figure 4:
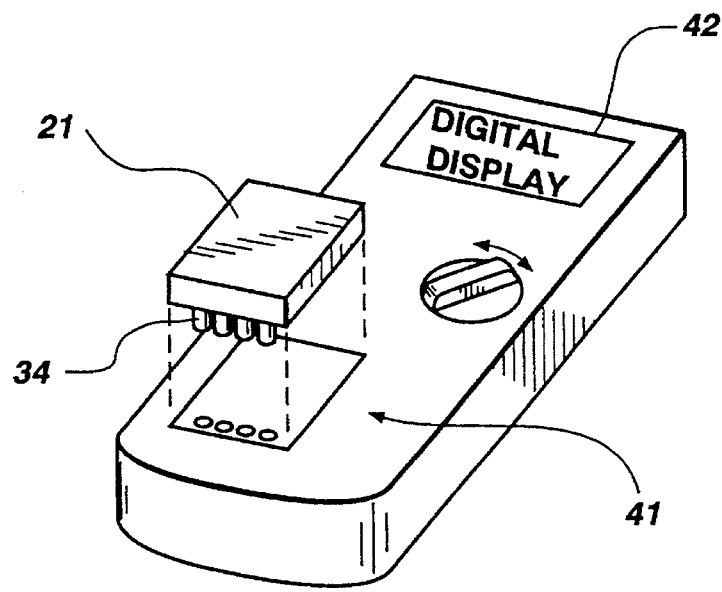
FIG. 4 shows an additional embodiment of the combined sensor and circuitry for implementing the subject invention.

The subject device can be correlated to the monitored polymer sample by numerous techniques. For example, a sample 40 of the polymer may be placed directly on the electrodes of the sensor as described in FIG. 3. This sensor can be permanently attached to the monitored polymer material so that the extent of polymerization can be checked at any time by merely inserting the pins 34 into a monitoring device 41 such as the hand held reader shown in FIG. 4. This reader 41 would contain the circuitry shown in FIG. 2, including a power supply for the signal generator. The reading is then displayed on the LCD 42, giving an accurate statement of condition for the batch of polymer to which the sample relates. This system could be readily applied with respect to batch shipments of adhesives, paints, caulks, and similar products which are stored and shipped in quantity. Once the reading is taken, the sensor 21 is returned to the material, to which it remains attached for future monitoring.

Figure 5:
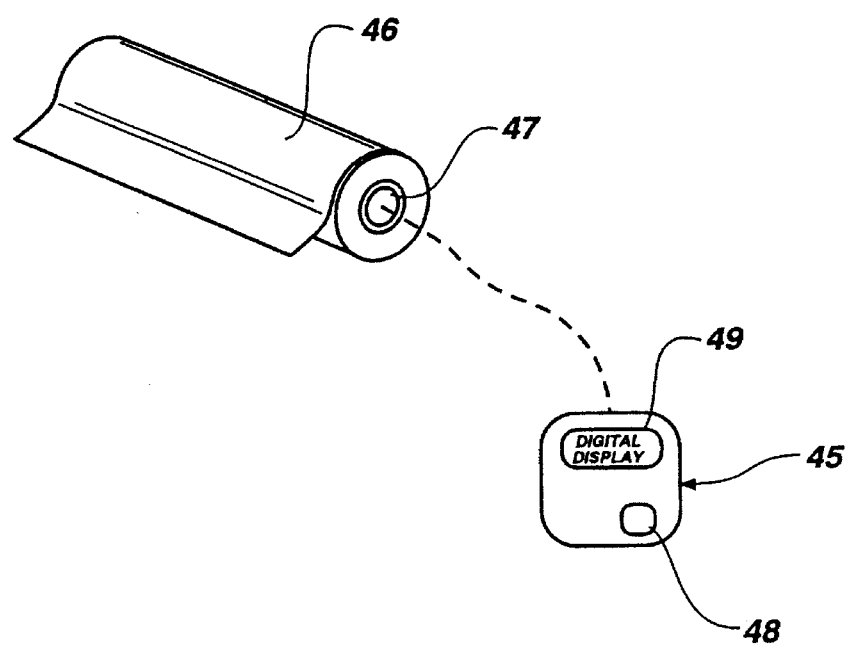
FIG. 5 discloses an additional embodiment of the subject invention, in combination with pre-preg material.

Alternately, the circuitry and sensor could be housed in a small, disposable unit such as that illustrated in FIG. 5. In this embodiment, the device 45 is a disposable unit which is coupled directly to the monitored polymer 46. Where the polymer 46 is prepreg material, the monitoring device 45 is loaded with a sample of representative polymer associated with the prepreg material 46. This device 45 is then permanently attached to the cardboard core 47 in visual position. When a reading is to be taken, the circuit may be activated by pressing a switch 48 which energizes the circuit and gives a reading on the LCD 49. In this manner, wherever the roll of prepreg material is shipped, its extent of polymerization can be immediately read from the attached device 45. It will be apparent that numerous methods of permanent or temporary attachment may be envisioned. These may include sensors which have a sample of material embedded at the time of manufacture, as in FIG. 3, or may be sensors which are inserted directly into the monitored polymer.

These features also suggest the use of the present invention as part of a more general method for monitoring extent of cross linking of polymer material which comprises the steps of (i) identifying polymer material in pre-cure stage; (ii) attaching a sensor in contact with the identified polymer as part of the material, which sensor enables intermittent or continuous reading of cure state of the polymer; and (iii) maintaining the sensor in contact with the polymer throughout the pre-cure stage of the polymer as a means for determining extent of cure of the material to which the sensor is attached. The same steps can be applied toward a batch of polymer material in pre-cure stage, wherein a sample of the polymer material is separated from the batch and the sensor is attached in contact with the sample of the identified polymer material. In this latter case, the material may be visually inaccessible, such as being in a closed container, but the sample which is attached to the outside of the container will be indicative of the contents. For this reason it is important that the sample being measured is fixed to the container so that the sample polymer experiences the same temperature and environmental conditions of the primary batch of polymer. The circuit described above could be in the form of a hand-held meter, which when attached to a sensor, would give a voltage proportional to the parameter of the material being measured.

It will be apparent to those skilled in the art that the foregoing disclosure is merely representative of preferred embodiments of the invention and is not to be considered limiting, except as set forth in the following claims.

We claim:

1. A method for detecting extent of cross-linking of a high impedance polymer material during a pre-cure stage, said method comprising the steps of:

a) applying a test signal through a sensor to the polymer material in the pre-cure stage to determine a level of impedance and corresponding sample voltage representative of a degree of cross-linking within the material;

b) applying the same test signal through the sensor to a reference resistance having a fixed resistance to determine a reference voltage;

c) determining a voltage difference between the test signal applied to the polymer at pre-cure stage and the test signal applied to the reference resistance as the reference voltage;

d) correlating the voltage difference as a relative indicator of the extent of cross-linking which has occurred within the polymer material, based on comparison of magnitude of the voltage difference with respect to a comparable potential range of impedance for the polymer material from its lower impedance stage at minimal cross-linking to its high impedance stage at maximum impedance for total cross-linking.

2. A method as defined in claim 1, wherein the voltage difference is processed by converting the voltage to direct current and inputting this direct current to a display device which gives direct readout of a value which can be correlated with the extent of cross-linking of the polymer.

3. A method as defined in claim 2, wherein the direct readout comprises a DC voltage ranging from approximately 0.5 volts at low impedance to 0.0 at high impedance, representing a range of magnitude of at least approximately $1 \times 10^4$.

4. A method as defined in claim 1, wherein the test signal is applied by generating a low frequency signal of less than 10 Hz, having a low amplitude of less than 20 volts peak to peak, and by applying this signal to the polymer in uncured stage and to the reference resistance.

5. A method as defined in claim 4, wherein the test signal is applied by generating a low frequency signal of approximately 0.1 Hz to 5 Hz, having a low amplitude of less than 10 volts peak to peak, and by applying this signal respectively to the polymer and the reference resistance.

6. A method as defined in claim 1, comprising the more specific step of applying the test signal to reference resistance comprising a fixed value resistor.

7. A method as defined in claim 1, wherein the steps of applying test signal to the polymer material and to the reference resistance comprise the specific steps of forming a voltage divider wherein the voltage output is proportional to the ratio of the impedance of the reference material to total impedance of the polymer material plus the reference resistance.

8. A method as defined in claim 1, wherein the steps comprise a process for measuring the extent of cross-linking in paint material, the method comprising the more specific step of applying paint to be tested to the sensor and processing the voltage difference in accordance with claim 1.

9. A method as defined in claim 1, wherein the steps comprise a process for measuring the extent of cross-linking in a dental polymer material, the method comprising the more specific step of applying dental polymer to be tested to the sensor and processing the voltage difference in accordance with claim 1.

10. A method of monitoring extent of cross-linking of polymer in a B-staged material in a pre-cure stage, comprising the steps of:

a) selecting a B-staged material which has an uncertain extent of cross-linking or an unknown state of curing; and b) applying a test signal through a sensor to the B-staged material in the pre-cure stage to determine a level of impedance and corresponding sample voltage representative of a degree of cross-linking within the material;

c) applying the same test signal through the sensor to a reference resistance having a fixed resistance to determine a reference voltage;

d) determining a voltage difference between the test signal applied to the B-staged material at pre-cure stage and the test signal applied to the reference resistance as the reference voltage;

e) correlating the voltage difference as a relative indicator of the extent of cross-linking which has occurred within the B-staged material, based on comparison of magnitude of the voltage difference with respect to a comparable potential range of impedance for the B-staged material from its lower impedance stage at minimal cross-linking to its high impedance stage at maximum impedance for total cross-linking.

11. A method as defined in claim 10, wherein the voltage difference is processed by converting the voltage to direct current and inputting this direct current to a display device which gives direct readout of a value which can be correlated with the extent of cross-linking of the polymer.

12. A method as defined in claim 11, wherein the direct readout comprises a DC voltage ranging from approximately 0.5 volts at lower impedance to 0.0 at high impedance, representing a range of magnitude of at least approximately $1 \times 10^4$.

13. A method as defined in claim 10, wherein the steps of applying test signal to the polymer material and to the reference resistance comprises the specific steps of forming a voltage divider wherein the voltage output is proportional to the ratio of the impedance of the reference material to total impedance of the polymer material plus the reference resistance.

14. A device for testing extent of cross-linking of a polymer material in a pre-cure stage, said device comprising:

a signal generator capable of generating a low frequency, low amplitude signal;

a sensor coupled to the signal generator and adapted for receiving a coating of the polymer material to be tested, said sensor having a known impedance;

a reference resistance which has a resistivity approximately equal to the geometric mean of (i) the impedance of the sensor with polymer material in its lower-resistivity state, and (ii) the expected impedance of the polymer material when the polymer material has reached its high resistivity state upon full curing;

voltage means for determining voltage difference between a signal detected through the sensor with polymer material and a signal detected through the sensor at the reference resistance; and converting means coupled to the voltage means for converting the voltage difference to a factor representing the extent of cross-linking which has occurred within the polymer material.

15. A device as defined in claim 14, wherein the signal generator produces a signal within the range of 0.1 Hz to 5 Hz with an amplitude of less than 20 volts peak to peak.

16. A device as defined in claim 15, wherein the signal generator comprises a sinusoidal signal generator having a peak to peak voltage of no greater than 10 volts.

17. A device as defined in claim 14, wherein the reference material comprises a fixed value resistor.

18. A device as defined in claim 14, wherein the sensor with polymer material and the reference material collectively comprise a voltage divider wherein the voltage output is proportional to the ratio of the impedance of the reference material to total impedance of the polymer material plus the reference material.

19. A device as defined in claim 18, further comprising a buffer circuit coupled to the voltage means, said buffer circuit providing means for raising the load impedance greater than $10^{15}$ Ohms to preventing loading the voltage divider output voltage.

20. A device as defined in claim 19, further comprising a filter stage coupled to the buffer circuit and including means to limit bandwidth reception of the device to reduce noise sensitivity.

21. A device as defined in claim 14, further comprising display means coupled to the converting means to provide a visual readout of the extent of cross-linking in real time mode.

22. A device as defined in claim 21, wherein said device is contained within a housing, said housing having an opening sufficiently large to enable insertion of a drop of polymer material to be tested, said housing being attached to a container of the polymer material as an indicator of extent of cross-linking in real time mode.

23. A device as defined in claim 22, wherein the housing and device are prepared as a disposable item to be discarded upon completion of use.

24. A device as defined in claim 21, wherein the sensor is prepared as a disposable item, said sensor including means for replaceable detachment from the device, said device being otherwise reusable except for the disposable sensor.

* * * * *